US005079263A

United States Patent [19]

[11] Patent Number: 5,079,263

[45] Date of Patent: Jan. 7, 1992

Zeeck et al.

[54] MANUMYCIN DERIVATIVES AND THE USE THEREOF

[75] Inventors: Axel Zeeck; Ralf Thiericke, both of Göttingen; Hans Zähner, Tübingen; Gerhard Dickneite; Hans H. Sedlacek, both of Marburg, all of Fed. Rep. of Germany

[73] Assignee: Behringwerke Aktiengesellschaft, Marburg/Lahn, Fed. Rep. of Germany

[21] Appl. No.: 278,885

[22] Filed: Dec. 2, 1988

[30] Foreign Application Priority Data

Dec. 4, 1987 [DE] Fed. Rep. of Germany ....... 3741056

[51] Int. Cl.[5] .............................................. A61K 31/17

[52] U.S. Cl. .................................... 514/616; 514/617; 514/619; 514/622; 564/156; 564/163; 564/167; 564/168; 564/170; 564/182

[58] Field of Search ............... 564/155, 157, 163, 156, 564/158, 167, 170, 182; 514/616, 617, 619, 622

[56] References Cited

PUBLICATIONS

Thiericke et al., *J. Chem. Soc. Perkin Trans. I,* 1988, (8), pp. 2123-2127.

F. Buzzetti et al., Pharm. Acta Helv. 38: 371-374, (1963).

Zeeck et al., J. of Antibiotics, vol. XL (11): 1530-1540, (1987).

Zeeck et al., J. of Antibiotics, vol. XL (11): 1541-1548, (1987).

R. Thiericke et al., J. of Antibiotics, vol. XL (11) 1549-1554, (1987).

Engelbrecht et al., Hoppe-Seyler's Z. Physiol. Chem. 363:305-315, (1982).

K. Nakajima et al., J. of Biol. Chem. 254 (10): 4027-4031, (1979).

*Primary Examiner*—Richard L. Raymond
*Assistant Examiner*—Scott C. Rand
*Attorney, Agent, or Firm*—Finnegan, Henderson, Farabow, Garrett, and Dunner

[57] ABSTRACT

I

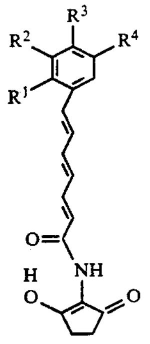

where
$R^1$ is H or OH;
$R^2$ is H or OH;
$R^3$ is H, OH, $OCH_3$, $CH_3$ or $NH_2$;
Rhu 4 is H, OH, $OCH_3$, $NH_2$ or

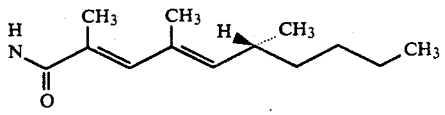

The compounds of the formula I are prepared by fermentation of the strain *Streptomyces parvulus* DSM 40722 in the presence of substituted benzoic acids of the general formula II

II

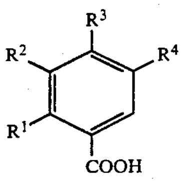

where
$R^1$ is H or OH;
$R^2$ is H or OH;
$R^3$ is H, OH, $OCH_3$, $CH_3$ or $NH_2$;
$R^4$ is H, OH, $OCH_3$ or $NH_2$, and they inhibit Leukocyte elastase and can be used as pharmaceuticals.

5 Claims, No Drawings

MANUMYCIN DERIVATIVES AND THE USE THEREOF

DESCRIPTION

The present invention relates to manumycin derivatives of the general formula I

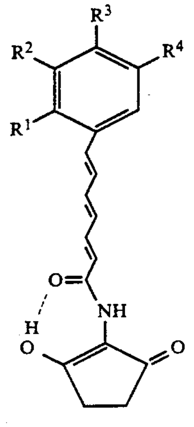

where
- $R^1$ is H or OH;
- $R^2$ is H or OH;
- $R^3$ is H, OH, $OCH_3$, $CH_3$ or $NH_2$;
- $R^4$ is H, OH, $OCH_3$, $NH_2$ or

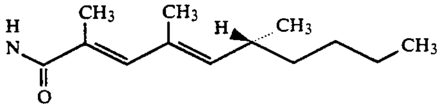

The present invention also relates to a process for the preparation of compounds of the general formula I, which comprises fermentation of the strain *Streptomyces parvulus* Tü 64 (DSM 40722) in the presence of substituted benzoic acids of the general formula II

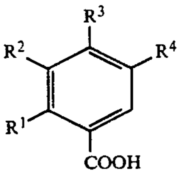

II where
- $R^1$ is H or OH;
- $R^2$ is H or OH;
- $R^3$ is H, OH, $OCH_3$, $CH_3$ or $NH_2$;
- $R^4$ is H, OH, $OCH_3$ or $NH_2$, in suitable nutrient media.

The compounds of the general formula I are derived from manumycin (formula III) which has been described by F. Buzzetti et al., (Phar. Acta. Helv., 1963, 38, 871) and whose structure and absolute configuration have been determined by A. Zeeck et al. (J. Antibiotics, 1987, 40, 1530 and 1549).

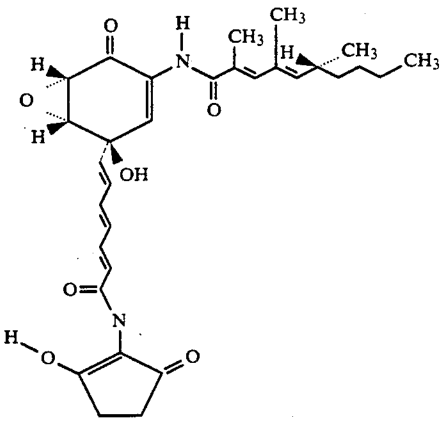

In order to avoid the normal biosynthesis of the central m-$C_7N$ starter unit for manumycin, non-physiological amounts of other $C_7$ precursor molecules were added to the culture medium during the stationary phase of growth of Streptomyces parvulus (DSM 40722). Besides a carbon and nitrogen source, the abovementioned culture medium contains the customary inorganic salts. Extraction of the mycelium with an organic solvent which is immiscible, or only slightly miscible, with water results in colored extracts from which compounds of the general formula I are obtained after removal of the lipophilic constituents and purification of the crude product by chromatography.

Hydrolysis of compounds of the general formula I with $R^4$=

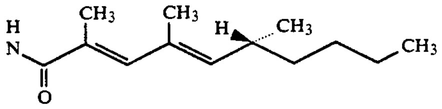

(side-chain of manumycin) with 20% strength methanolic KOH produces compounds of the general formula I with $R^4$=$NH_2$. The compounds (1) and (2) from Table 1 can also be obtained by reduction of manumycin (formula III) by known processes, such as described by A. Zeeck et al. (J. Antibiotics, 1987, 40, 1541). We have found that compounds of the general formula I, especially the compounds (1), (2), (3) and (5) in Table 1, inhibit leukocyte elastase.

TABLE 1

| | Compounds of the general formula I with the following radicals $R^1$ to $R^4$ | | | |
|---|---|---|---|---|
| | $R^1$ | $R^2$ | $R^3$ | $R^4$ |
| Compound (1) | OH | H | OH | 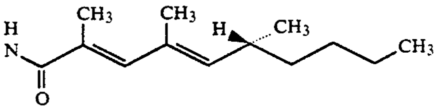 |

TABLE 1-continued

| | Compounds of the general formula I with the following radicals $R^1$ to $R^4$ | | | |
|---|---|---|---|---|
| | $R^1$ | $R^2$ | $R^3$ | $R^4$ |
| Compound (2) | H | H | OH | 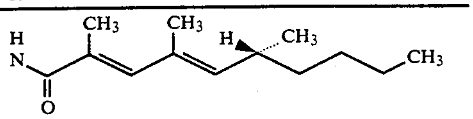 |
| Compound (3) (= 64-mABA) | H | H | H | 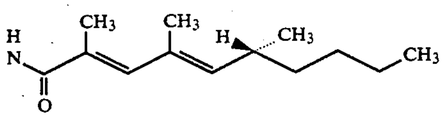 |
| Compound (4) | H | H | H | $NH_2$ |
| Compound (5) (= 64-pABA) | H | H | $NH_2$ | H |

Leukocyte elastase, which is one of the neutral proteases, is involved in the human or animal body in the degradation of a very wide variety of soluble and tissue-associated proteins.

Since, however, uncontrolled proteolytic activity would result in the degradation of important regulatory proteins (such as those of the coagulation and complement systems), under physiological conditions the body maintains a balance between the enzyme and its naturally occurring inhibitors (such as, for example, α1-protease inhibitor, α2-macroglobulin). In various pathological states there may now be an increased secretion of elastase from leukocytes (preferentially from polymorphonuclear granulocytes) or a decreased release of inhibitors, and thus destruction of important regulatory or structural proteins.

The syndromes with this etiology are many and various and may affect a variety of organs and tissues; they include the various states of shock (for example septic shock), disturbances of the coagulation system, lung disorders, such as acute respiratory distress syndrome (ARDS) and pulmonary emphysema, post-traumatic and postoperative complications, various types of inflammation, both in its acute and in its chronic form, such as rheumatoid arthritis and other collagenoses.

Furthermore, elastase secreted by tumor cells plays an important part in metastasis and the invasive growth of tumors in that it destroys the basement membrane surrounding the primary tumor and facilitates the passage of tumor cells through this matrix.

Accordingly, the use of elastase inhibitors is of therapeutic benefit in all the disorders described.

The invention is explained in detail in the examples which follow.

EXAMPLE 1

Preparation of 64-mABA

(Compound (3), see Table 1)

a) Preparation of a suspension of spores of the producer strain 100 ml of nutrient solution (4 g of yeast extract, 10 g of malt extract, 4 g of glucose, 1 l of tapwater, pH before sterilization 7.3) in a 500 ml Erlenmeyer flask with septum inlet are inoculated with the strain DSM 40722 and incubated on a rotating shaker at 250 rpm at 28° C. for 72 hours. Subsequently, 20 ml of culture liquid are uniformly distributed in a 500 ml Roux flask containing the nutrient medium of the abovementioned composition, to which 20 g of agar have been added per liter for solidification, and are decanted. The cultures are incubated at 28° C. for 10 to 14 days. The spores which have been produced after this time in each Roux flask are rinsed out with 500 ml of deionized water, which contains one drop of a commercially available nonionic surfactant, and are immediately used further or stored at −22° C.

b) Preparation of a culture or preculture of the producer strain in an Erlenmeyer flask A 500 ml Eerlenmeyer flask with septum inlet, containing 100 ml of a nutrient solution composed of 2% defatted soybean meal, 2% mannitol and water ad 100 ml (pH 7.5 before autoclaving) is inoculated with a culture grown in a slant tube or with 0.2 ml of spore suspension, and is incubated on a shaker at 250 rpm at 28° C. Sufficient for the inoculation of 10, 20, 25 and 100 l fermenters is a 48-hour old submerged culture (5%) from the same nutrient solution.

c) Fermentation

A fermenter of 15 l capacity is operated as follows. 4 l of air per minute are passed into the culture liquid at an incubation temperature of 28° C. and at 250 rotations per minute (medium: defatted soybean meal 2%, mannitol 2%, pH of the solution adjusted to 7.5 with NaOH before sterilization). Foam formation can be suppressed by repeated addition of a few drops of ethanolic polyol solution. After 30–45 hours, preferably 36 hours, 55 mmol of 3-aminobenzoic acid (dissolved in a little water, pH=7) per liter of culture medium are added. After a further 38 hours, the culture is adjusted to pH 4.5 with 2M HCl, stirred with Hyflo Celite (50 g per liter) for 10 minutes and filtered. The filter residue is extracted three times with acetone (250 ml per liter of culture solution), and the culture filtrate is extracted three times with ethyl acetate: the extracts are concentrated. The aqueous-oily residues are combined and extracted four times with chloroform (30 ml per liter of culture solution). The combined organic phase yield, after evaporation of the solvent, an oily crude product which solidifies on treatment with ice-cold petroleum ether. The dark brown amorphous powder is chromatographed twice on Sephadex LH-20 columns (100×2.5 cm, agent for application and elution: $CHCl_3$). This is followed by chromatography on an RP-8 silica gel column (acetonitrile/water, 3:1 v/v) in order to yield, after an optimal fermentation, 123 mg/l of culture broth of pure yellow amorphous 64-mABA (compound (3)). The melting point is 196°–197° C.

Other properties are as follows $[\alpha]_D^{22}$ is $-213°$ ($c=0.15$ in $CHCl_3$) IR (KBr): 3420, 3260, 2940, 2910, 1605, 1575(sh) 1530 and 996 $cm^{-1}$ UV spectrum: $\lambda_{max}$(Methanol)=351 (40 800), 263 (25 100)

$^{13}C$, 1H-NMR (200 MHz, $CDCl_3$): $_c$=197.4 (s, C-1''), 174.3 (C-3''), 168.7 (s, C-1'), 165.9 (s, C-13), 144.0 (d, C-11), 142.1 (d, C-5'), 141.6 (d, C-9), 138.9 (d, C-3'), 138.8 (s, C-2), 137.4 (s, C-4), 136.9 (d, C-7), 130.2 (d, C-10), 130.1 (s, C-2'), 129.4 (s, C-4'), 129.3 (d, C-6), 128.5 (d, C-8), 123.0 (d, C-5), 120.4 (d, C-12), 120.1 (d, C-1), 118.0 (d, C-3), 115.3 (s, C-2''), 37.1 (t, C-7'), 32.8 (d, C-6'), 32.2 (t, C-5''), 29.8 (t, C-8'), 25.7 (t, C-4''), 22.8 (t, C-9'), 20.8 (q, C-13'), 16.6 (q, C-12'), 14.4 (q, C-10'), 14.1 (q, C-11'), $\delta_H$ ($CDCl_3$), 0.86 (t, H 6.4 Hz, 10'-$H_3$), 0.93 (d, J 6.4 Hz, 13'-$H_3$), 1.14–1.42 (m, broad, 7'-$H_2$, 8'-$H_2$, 9'-$H_2$), 1.84 (d, j 1.6 Hz, 12'-$H_3$), 2.12 (d, j 1.6 Hz, 11'-$H_3$), 2.34–2.50 (m, broad, 6'-H), 2.58–2.60 (s, broad, 4''-$H_2$, 5''-$H_2$), 5.36 (d, j 10 Hz, 5'-H), 6.09 (d, j 15 Hz, 12-H), 6.42 (dd, j 13.5 and 12 Hz, 10-H), 6.62–6.88 (m, 7-H, 9-H, including 6.82, 3'-H), 6.90 (dd, j 15.5 and 11 Hz, 8-H), 7.15 (d, broad j 7.5 Hz, 5-H), 7.22–7.46 (m, 1-H, 11-H), 11-H), 7.64 (s, broad, NH), 7.86 (s, 3-H), 7.88 (s, broad, NH), 13.80 (s, broad, OH);

Mass spectroscopy: m/z 502. (21%, $M^+$, found: 502.2832 for $C_{31}H_{38}N_2O_4$) 417 (24%), 324 (11%), 193 (38%), 123 (11%), 109 (64%).

Elemental analysis: C, 74.04; H, 7.81; N, 5.49. $C_{31}H_{38}N_2O_4$ requires C, 74.06; H, 7.62, N, 5.57.

EXAMPLE 2

Preparation of Compound (4) in Table 1 by Hydrolysis of 64-mABA 94 mg of 64-mABA were dissolved in 50 g of 20% strength methanolic KOH and refluxed for 24 hours. The yellow reaction mixture was adjusted to pH 2 with aqueous oxalic acid and extracted twice with 300 ml of $CHCl_3$. The combined organic extracts were dried with $Na_2SO_4$ and evaporated, resulting in a yellow amorphous powder. This crude product yielded after column chromatography on silica gel (45 cm×2.5 cm, $CHCl_3$/MeOH, 9:1 v/v) three main products:

(a) 5.8 mg starting material,
RF=0.60 ($CHCl_3$/MeOH, 9:1 v/v)

(b) 30 mg pale yellow oil,
RF=0.43 ($CHCl_3$/MeOH, 9:1 v/v )

(c) 34.2 mg yellow powder,
RF=0.39 ($CHCl_3$/MeOH, 9:1 v/v )

(b) yielded after further purification on a Sephadex LH-20 column (45 cm×2.5 cm, $CHCl_3$) 20.0 mg (54%) of 2,4,6-trimethyl-2,4-decadienoic acid (formula IV)

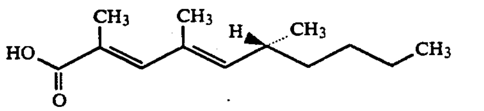

(IV)

Product (c) yielded after chromatography on a Sephadex LH-20 column (50 cm×2.5 cm, $CHCl_3$) 302 mg (55%) of compound (4) as a yellow amorphous powder with the following properties:

Melting point: 256° C.

IR (KBr): 3440, 3380, 3260, 1680 (sh) 1610, 1550 and 1008 $cm^{-1}$.

UV spectrum in methanol: $\lambda_{max}$=342 (44 500), 259 (24 600).

$^{13}C$, $^1H$-NMR (200 MHz, DMSO-$d_6$): $\delta_H$ 2.09 (s, 4''-$H_2$), 2.48 (s, 5''-$H_2$), 3.30 (s, broad, NH, overlapped by HOD), 6.43–7.08 (m, 9 protons), 7.29 (dd, J 15.0 and 12.5 Hz, 11-H), 991 (s, broad, OH); $\delta_C$ 166.1 (s, C-13), 148.8 (s, C-2), 142.5 (d, C-11), 137.3 (d, C-9), 136.9 (d, C-7), 129.9 (s, C-4), 114.8 (s, C-2''), 28.8 (t, broad, C-4''), C-5''), the signals 129.1 (d), 127.4 (d), 121.2 (d), 119.0 (d), 114.9 (d), 114.6 (d) and 112.5 (d) could not be assigned unambiguously to C-1, C-3, C-5, C-6, C-8, C-10 and C-12, and the signals for C-1'' and C-3'' were not observed.

Mass spectrometry: m/z 310 (13%, $M^+$, found: 310.1317 for $C_{18}H_{18}N_2O_3$), 198 (49%), 180 (15%), 170 (92%), 132 (100%).

EXAMPLE 3

Preparation of 64-pABA (Compound (5) in Table 1)

55 mmol/liter 4-aminobenzoic acid were fed to a 36-hour old culture of Streptomyces parvulus DSM 40722 (conditions as in 1c). The extractions of the mycelium and culture filtrate after 74 hours were carried out as described above. The dark brown crude product yielded after column chromatography twice on silica gel (30 cm×5 cm, $CHCl_3$/MeOH, 9:1 v/v) 35.8 mg/liter 64-pABA (compound (5)) as a yellow amorphous powder with the following properties:

Melting point: 242° C.

IR (KBr): 3440, 3350, 3240, 2930, 2860, 1710 sh, 1615 sh, 1585, 1000 $cm^{-1}$.

UV spectrum in methanol: 392 (31 500), 261 (14 400), 201 (15 200) $^{13}C$, $^1H$ NM(200 MHz, DMSO-$d_6$): $^{\delta}C$ 166.4 (s, C-13), 149.6 (s, C-1), 143.1 (d, C-11), 142.5 (d, C-9), 137.8 (d, C-7), 128.3 (d, C-3 and C-5), 127.3 (d, C-10), 124.1 (s, C-4), 122.9 (d, C-8), 119.4 (d, C-12), 114.9 (s, C-2''), 113.8 (d, C-2 and C-6), 28.8 (t, broad, C-4'' and C-5''); the signals for C-1'' and C-3'' could not be observed.

$\delta_H$ 2.10 (s, 4''-$H_2$), 2.47 (s, 5''-$H_2$), 3.30 (s, broad, NH, overlapped by HOD), 5.50 (s, broad, NH), 6.34–6.94 (m, 7 protons, including 6.57 (d, J 8.5 Hz, 2-H and 6-H)), 7.23 (d, J 8.5 Hz, 3-H and 5-H), 7.30 (dd, J 14.5 and 12 Hz, 11-H), 9.94 (s, broad, OH);

Mass spectrometry: m/z 310 (8.4% $M^+$ Found: 310.1317 for $C_{18}H_{18}N_2O_3$) 198 (10.4%), 170 (40.7%), 132 (100%).

EXAMPLE 4

Assay for Elastase from Polymorphonuclear Granulocytes (PMN Elastase)

The elastase was isolated from human leukocytes by the method described by Engelbrecht et al. (Hoppe-Seyler's Physiol. Chem. 363, pp. 305–315, 1982). The substrate used was the MeO-Suc-Ala-Ala-Pro-Val-pNA (Calbiochem) described by Nakajima et al. (J. Biol. Chem. 254, pp. 4027–4032, 1979). The Liberation of the p-nitroaniline from the substrate in 15 minutes was measured as the increase in absorption at 405 nm in a spectrophotometer. This absorption was defined as 100% activity of the enzyme PMN elastase. The inhibitors of PMN elastase were preincubated in increasing concentrations up to a maximum of 100 μg/ml with the enzyme for 1 hour, and the enzyme reaction was started with the substrate. The $IC_{50}$ was defined as that inhibitor concentration which inhibits 50% of the enzyme activity. Substances which showed no inhibiting effect at the maximum concentration of 100 μg/ml were defined as inactive.

The $IC_{50}$ values obtained are compiled in Tab. 2. The activity of the reference compound manumycin is comparable to that of the compounds (1) to (3), whereas compound (5) has a distinctly weaker inhibiting effect. Compound (4) is inactive in this assay.

TABLE 2

Inhibiting effect of manumycin and the tested manumycin derivatives on PMN elastase

| Substance | $IC_{50}$ (μg/ml) |
|---|---|
| Manumycin (formula III) | 4.4 |
| Compound (1) | 2.5 |
| Compound (2) | 3.1 |
| Compound (3) (= 64-mABA) | 3.6 |
| Compound (4) | — |
| Compound (5) (= 64-pABA) | 42.0 |

We claim:

1. A compound of the formula I

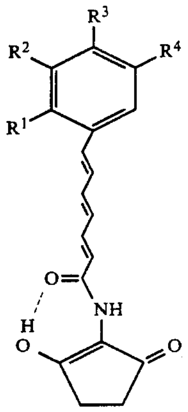

where $R^1$ is H or OH;

$R^2$ is H or OH;

$R^3$ is H, OH, $OCH_3$, $CH_3$ or $NH_2$;

$R^4$ is H, OH, $OCH_3$, $NH_2$ or

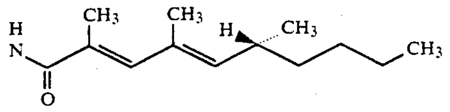

with the exception of compound (1) with $R_1$=OH, $R_2$=H, $R_3$=OH and $R_4$ = 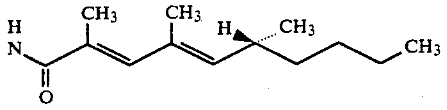

and of compound (2) with $R_1$=H, $R_2$=H, $R_3$=OH and $R_4$ = 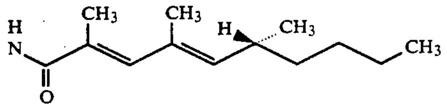

and of compound (4) with $R_1=R_2=R_3$=H, and $R_4$ is $NH_2$.

2. A compound of the formula I, where $R_1=R_2=R_3$=H, and $R^4$ is

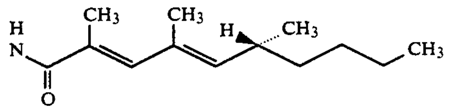

3. A compound of the formula I, where $R_1=R_2=R_4$=H, and $R_3$ is $NH_2$.

4. A pharmaceutical composition for the inhibition of elastase comprising an effective amount of a compound of formula I as claimed in claim 1 or a salt thereof together with a pharmaceutically acceptable carrier.

5. A method for inhibiting elastase comprising contacting said elastase with a compound of formula I as claimed in claim 1.

* * * * *